United States Patent [19]

Sanderson et al.

[11] Patent Number: 5,105,037

[45] Date of Patent: * Apr. 14, 1992

[54] PROCESS FOR CO-OLIGOMERIZING PROPYLENE AND ALPHA-OLEFINS TO PREPARE SYNTHETIC LUBRICANT BASE STOCKS HAVING IMPROVED PROPERTIES

[75] Inventors: John R. Sanderson, Leander; Edward T. Marquis, Austin, both of Tex.

[73] Assignee: Texaco Chemical Company, White Plains, N.Y.

[*] Notice: The portion of the term of this patent subsequent to Oct. 1, 2008 has been disclaimed.

[21] Appl. No.: 522,941

[22] Filed: May 14, 1990

[51] Int. Cl.$^5$ .............................................. C07C 2/02
[52] U.S. Cl. ..................................... 585/533; 585/258
[58] Field of Search ................................ 585/533, 258

[56] References Cited

U.S. PATENT DOCUMENTS

| | | |
|---|---|---|
| 2,951,087 | 8/1960 | Hauser et al. |
| 3,412,039 | 11/1968 | Miller |
| 3,432,571 | 3/1969 | Noddings et al. |
| 3,459,815 | 8/1969 | Noddings et al. |
| 3,845,150 | 10/1974 | Tsoung-Yuan et al. |
| 3,849,507 | 11/1990 | Zuech |
| 4,153,638 | 5/1979 | Bercik et al. |
| 4,299,730 | 11/1981 | Sommer et al. |
| 4,351,980 | 9/1982 | Reusser et al. |
| 4,380,509 | 4/1983 | Sommer et al. |
| 4,456,779 | 6/1984 | Owen et al. |
| 4,480,142 | 10/1984 | Cobb |
| 4,531,014 | 7/1985 | Gregory et al. |
| 4,604,491 | 8/1986 | Dressler et al. |
| 4,808,559 | 2/1989 | Sommer et al. |
| 4,827,064 | 5/1989 | Wu |
| 4,879,425 | 11/1989 | Kukes et al. |

OTHER PUBLICATIONS

"The Chemistry of Catalytic Hydrocarbon Conversions", Pines Academic Press, 1981, p. 33.

Kuliev et al., "Preparation of High-Viscosity Synthetic Lubricants Using an Aluminosilicate Catalyst" Institute of Petrochemical Processing of the Academy of Sciences of the Azerbaidzhan S SR, *Azerbaidzhanskoes, Niftiano, Khoziaistro*, 1983, No. 4, pp. 40–43.

Figueras, "Pillared Clays as Catalysts", *Catal. Rev. Sci. Eng.* 30, pp. 457-499 (1988).

Friedlander, "Organized Polymerization. I. Olefins on a Clay Surface," *Journal of Polymer Science:* Part C, No. 4, pp. 1291-1301.

Friedlander et al., "Organized Polymerization III. Monomers Intercalated in Montmorillonite," *Polymer Letters*, vol. 2, pp. 475-479 (1960).

"Intercalated Catalysts and Pillared Clays," from a Process Evaluation Research Planning Report, Chem. Systems Titled Catalysts, Selected Developments, 84-3, pp. 239-249 (Dec. 1985).

Bolan, "Synthetic Lubricant Base Stocks", Process Economics Program Report No. 125A, SRI International, Apr. 1989 and Supplement A, Sep. 1989.

"Synthetic Lubricants from Internal Olefins," Process Evaluation/Research Planning Report Chem. Systems, 84-Q-1, pp. 17-45.

Adams, "Synthetic Organic Chemistry Using Pillared, Cationed-Exchanged and Acid-Treated Montmorillonite Catalysts, A Review," *Applied Clay Science*, 2 (1987) pp. 309-342.

Adams et al., "Clays as Selective Catalysts in Organic Synthesis", Journal of Inclusion Phenoma, vol. 5 (1987), pp. 663-674.

Chauduri and Sharma, "Some Novel Aspects of the Dimerization of L-Methylstyrene with Acidic Ion-Exchange Resins, Clays, and Other Acidic Materials as Catalysts," *Ind. Eng. Res.* vol. 28, pp. 1757-1763 (1989).

Purnell, "Catalysis by Ion-Exchanged Montmorillonites," *Catalysis Letters* 5 (1990) pp. 203-210.

*Primary Examiner*—Patrick P. Garvin
*Assistant Examiner*—E. D. Irzinski
*Attorney, Agent, or Firm*—Jack H. Park; Russell R. Stolle; Kenneth R. Priem

[57] ABSTRACT

A process is disclosed for preparing synthetic lubricant base stocks having improved properties. Synthetic lubricant base stocks may be prepared in good yield by oligomerizing linear olefins using certain acidic calcium montmorillonite clay catalysts. When a mixture of propylene and long-chain alpha-olefin is used, in which up to about 20 wt. % of the mixture comprises propylene, and the co-oligomers prepared therefrom are hydrogenated, a synthetic lubricant base stock having a lower pour point and a higher viscosity index is prepared.

40 Claims, No Drawings

PROCESS FOR CO-OLIGOMERIZING PROPYLENE AND ALPHA-OLEFINS TO PREPARE SYNTHETIC LUBRICANT BASE STOCKS HAVING IMPROVED PROPERTIES

CROSS-REFERENCE TO RELATED APPLICATIONS

This application is related to U.S. patent application Ser. No. 07/500,631, filed Mar. 28, 1990 now U.S. Pat. No. 5,053,569, which relates to the preparation of synthetic lubricant base stocks by oligomerizing linear olefins by means of certain acidic montmorillonite clays, and to co-pending U.S. patent application Ser. No. 07/516,931, filed Apr. 30, 1990, which relates to the preparation of synthetic lubricant base stocks having improved properties, made by oligomerizing mixtures of internal and alphaolefins by means of certain acidic montmorillonite clays. This application also relates to co-pending U.S. patent application Ser. No. 07/516,870, filed Apr. 30, 1990, which relates to synthetic lubricant base stocks made by oligomerizing linear olefins by means of certain aluminum nitrate-treated acidic montmorillonite clays. The totality of each of these three applications is incorporated herein by reference.

BACKGROUND OF THE INVENTION

1. Field of the Invention

The invention relates to the preparation of synthetic lubricant base stocks, and more particularly to synthetic lubricant base stocks having improved properties, made by co-oligomerizing propylene and long-chain alpha-olefins by means of certain acidic montmorillonite clay catalysts.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (Cst) at 100° C. Those base stocks with viscosities less than or equal to about 4 Cst are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution byproduct by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater. In addition to being excellent catalysts, these clays are non-hazardous and non-polluting. With respect to the present invention, Applicants have found, surprisingly, that synthetic lubricant base stocks with a lower pour point and an improved viscosity index may be obtained where the oligomers are prepared by co-oligomerizing a mixture of up to about 20 wt. % propylene and more than about 80 wt. % long-chain alpha-olefin in the presence of these clay catalysts. Additionally, incorporating the propylene lowers the cost of producing the base stocks by replacing a portion of the more expensive long-chain olefin feed with propylene.

SUMMARY OF THE INVENTION

The invention relates to a process for the preparation of oligomers, comprising contacting a mixture of propylene and an alpha-olefin containing at least 10 carbon atoms with a catalyst comprising an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater, in which the mixture of propylene and alpha-olefin is comprised of up to about 20 wt. % propylene.

DESCRIPTION OF THE PREFERRED EMBODIMENTS

Applicants discovered that synthetic lubricant base stocks may be prepared in good yield by oligomerizing long-chain olefins using certain acidic montmorillonite clay catalysts. Applicants have further discovered that certain properties of these synthetic lubricant base stocks are improved when the olefin feed comprises a mixture of alpha-olefin and up to about 20 wt. % propylene. Preferably, the mixture of alpha-olefin and propylene contains from about 2 to about 0 wt. % propylene. When oligomers produced in this manner are hydrogenated, they yield synthetic lubricant base stocks having a lower pour point. This is a desirable characteristic for most lubricating applications. Additionally, where the propylene comprises no more than about 15 wt. % of the long-chain alpha-olefin/propylene mixture, the resulting synthetic lubricants have a higher viscosity index, another desirable feature. A higher viscosity index indicates that the synthetic lubricant will be less susceptible to a change in viscosity when subjected to a change in temperature.

The long-chain alpha-olefin monomer feed stocks used in the present invention may be selected from compounds having the formula $R''CH=CH_2$, where $R''$ is an alkyl radical of 8 to 22 carbon atoms. A preferred range for the total number of carbon atoms in any one alpha-olefin molecule is 12 to 18, inclusive, with an especially preferred range being 13 to 16, inclusive. Mixtures of alpha-olefins having different numbers of carbon atoms may be used, provided that the total number of carbon atoms in any one alpha-olefin shall be within the range of 10 to 24, inclusive. The alpha-olefins and propylene to be co-oligomerized in this invention may be obtained by processes well-known to those skilled in the art and are commercially available.

The oligomerization reaction may be represented by the following general equation:

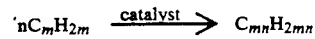

where n represents moles of monomer and m represents the number of carbon atoms in the monomer. Thus, the oligomerization of 1-decene may be represented as follows:

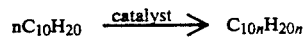

The co-oligomerization of propylene and I-decene may be represented as follows:

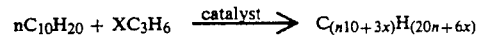

where n represents moles of long-chain alpha-olefin and x represents moles of propylene.

The reactions occur sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

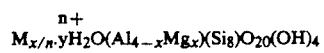

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 $M^2/g$ or greater. Illustrative examples include Filtrol grade 24, having a moisture content of 12 wt. %, a residual acidity of 8.5 mg KOH/g, and a surface area of 425 $M^2/g$; Filtrol grade 124, having a moisture content of 2 wt. %, a residual acidity of 7.0 mg KOH/g, and a surface area of 400 $M^2/g$; Filtrol grade 13, having a moisture content of 16 wt. %, a residual acidity of 15 mg KOH/g, and a surface area of 300 $M^2/g$; Filtrol grade 113, having a moisture content of 4 wt. %, a residual acidity of 10 mg KOH/g, and a surface area of 300 $M^2/g$; and Filtrol grade 224, having virtually no moisture, and having a residual acidity of 3.0 mg KOH/g, and a surface area of 350 $M^2/g$.

Preferably, the catalyst is activated by heat treatment before running the reaction. Applicants found, surprisingly, that heat treatment of the catalyst prior to running the oligomerization reaction causes the catalyst to be more active and produce a higher olefin conversion. Additionally, clays heat-treated in this manner are more stable, remaining active during the oligomerization reaction for a longer period of time. The clays may be heat-treated at temperatures in the range of about 50° to 400° C., with or without the use of a vacuum. A more preferred temperature range is 50° to 300° C. Optionally, an inert gas may be used during heat treatment as well. Preferably, the clay should be heat-treated under conditions and for a length of time which will reduce the water content of the clay to approximately 1 wt. % or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 150° to 180 ° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

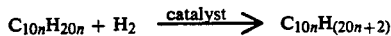

$$C_{10n}H_{20n} + H_2 \xrightarrow{catalyst} C_{10n}H_{(20n+2)}$$

where n represents moles of monomer used to form the oligomer. Hydrogenation of propylene/1-decene co-oligomers may be represented as follows:

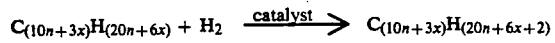

$$C_{(10n+3x)}H_{(20n+6x)} + H_2 \xrightarrow{catalyst} C_{(10n+3x)}H_{(20n+6x+2)}$$

where n and x represent moles of long-chain alpha-olefin and propylene, respectively, used to form the co-oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The monomer stripping step should be conducted under mild conditions. Distillation at temperatures exceeding 210° C. may cause the oligomers to break down in some fashion and come off as volatiles. Preferably, therefore, the reboiler or pot temperature should be kept at or under about 180° C. when stripping out the monomer.

The invention will be further illustrated by the following examples, which are given by way of illustration and not as limitations on the scope of this invention. The entire text of every patent, application or other reference mentioned herein is incorporated herein by reference.

EXAMPLES

The examples detailed in the table below demonstrate the use of the present invention in batch reaction systems:

Co-oligomerization Procedure

1-Tetradecene and catalyst (Harshaw/Filtrol Clay grade 124) were charged to a 1 liter autoclave, and the autoclave sealed. Propylene was pressured in and the mixture was heated to 160° C. for five hours. The pressure, due to the propylene, dropped slowly during the run. At the end of the run, the mixture was cooled to ambient temperature, a small amount of propylene was vented, and the mixture was filtered with suction. Analysis of the reaction mixture by high pressure liquid chromatography showed the presence of dimers, trimers, and higher oligomers. Percent conversions obtained and dimer/trimer ratios are shown in the attached table.

Hydrogenation of Co-oligomers

An autoclave was charged with finely powdered nickel catalyst and co-oligomer prepared according to the procedure outlined above. The autoclave was flushed with hydrogen and then pressured to 1000 psig with hydrogen. The mixture was heated to 200° C. and stirred at this temperature for 4 hours. The mixture was then repressured with hydrogen to 2000 psig as needed. The mixture was then cooled to ambient temperature, the catalyst was filtered and the monomer was removed. Properties of the reduced co-oligomers are recorded in the table below.

CO-OLIGOMERIZATION OF PROPYLENE AND 1-TETRADECENE USING H/F CLAY-124

| EX. NO. | PROPYLENE (% BY WT. OF OLEFIN MIXTURE) | % CON. OF $C_{14}$ ALPHA-OLEFIN | D/T + RATIO | TGA-% REMAINING AT 250° C. | VIS. AT 210° F. (Cst) | VI | POUR POINT (°F.) |
|---|---|---|---|---|---|---|---|
| 1 | 5 | — | — | 85.0 | 5.13 | 133 | −35 |
| 2 | 10 | 61.6 | 2.87 | 79.0 | 4.67 | 123 | −40 |
| 3 | 15 | 52.4 | 4.50 | 81.5 | 4.68 | 122 | −35 |
| 4 | 20 | 43.8 | 6.02 | 84.2 | 4.44 | 115 | −40 |
| 5 | 0 | 78.3 | 1.65 | 88.5 | 6.61 | 121 | −20 |

Con. = Conversion; D = Dimer; T+ = Trimer, plus Tetramer, Pentamer, etc; TGA = Thermogravimetric Analysis; Vis. = Viscosity; and VI = Viscosity Index.
Properties were determined on reduced bottoms.

We claim:

1. A process for the preparation of oligomers, comprising contacting a mixture of propylene and an alpha-olefin having from 10 to 24 carbon atoms, in which the mixture of propylene and alpha-olefin is comprised of up to about 20 wt. % propylene, with a catalytically effective amount of an acidic calcium montmorillonite clay having a moisture content ranging up to about 20 wt. %, a residual acidity in the range of about 3 to about 30 mg KOH/g, and a surface area of about 300 M²/g or greater.

2. The process of claim 1, wherein the alpha-olefin contains from 12 to 18 carbon atoms.

3. The process of claim 1, wherein the alpha-olefin contains from 12 to 18 carbon atoms and wherein the clay, before being contacted with the propylene and alpha-olefin mixture, is heat-treated to a moisture content of about 1 wt. % or less.

4. The process of claim 1, wherein the mixture of propylene and alpha-olefin is comprised of about 2 to about 10 wt. % propylene.

5. The process of claim 1, wherein the moisture content of the clay is about 12 wt. %, the residual acidity is about 8.5 mg KOH/g, and the surface area is about 425 M²/g.

6. The process of claim 1, wherein the moisture content of the clay is about 2 wt. %, the residual acidity is about 7.0 mg KOH/g, and the surface area is about 400 M²/g.

7. The process of claim 1, wherein the moisture content of the clay is about 16 wt. %, the residual acidity is about 15 mg KOH/g, and the surface area is about 300 M²/g.

8. The process of claim 1, wherein the moisture content of the clay is about 4 wt. %, the residual acidity is about 10 mg KOH/g, and the surface area is about 300 M²/g.

9. The process of claim 1, wherein the moisture content of the clay is essentially nil, the residual acidity is about 3.0 mg KOH/g, and the surface area is about 350 M²/g.

10. The process of claim 1, wherein the olefin mixture is contacted with the clay at a temperature of about 150° to about 180° C.

11. A process for the preparation of oligomers, comprising contacting a mixture of propylene and an alpha-olefin having from 12 to 18 carbon atoms, in which the mixture of propylene and alpha-olefin is comprised of up to about 20 wt. % propylene, with a catalytically effective amount of an acidic montmorillonite clay having a moisture content ranging up to about 20 wt. %, a residual acidity in the range of about 3 to about 30 mg KOH/g, and a surface area of about 300 M²/g or greater.

12. The process of claim 11, wherein the mixture of propylene and alpha-olefin is comprised of about 2 to about 10 wt. % propylene.

13. The process of claim 11, wherein the moisture content of the clay is about 12 wt. %, the residual acidity is about 8.5 mg KOH/g, and the surface area is about 425 M²/g.

14. The process of claim 11, wherein the moisture content of the clay is about 2 wt. %, the residual acidity is about 7.0 mg KOH/g, and the surface area is about 400 M²/g.

15. The process of claim 11, wherein the moisture content of the clay is about 16 wt. %, the residual acidity is about 15 mg KOH/g, and the surface area is about 300 M²/g.

16. The process of claim 11, wherein the moisture content of the clay is about 4 wt. %, the residual acidity is about 10 mg KOH/g, and the surface area is about 300 M²/g.

17. The process of claim 11, wherein the moisture content of the clay is essentially nil, the residual acidity is about 3.0 mg KOH/g, and the surface area is about 350 M²/g.

18. The process of claim 11, wherein the olefin mixture is contacted with the clay at a temperature of about 150° to about 180 ° C.

19. The process of claim 11, wherein the clay, before being contacted with the olefins, is heat-treated to a moisture content of about 1 wt. % or less.

20. The process of claim 11, wherein the olefin contains from 13 to 16 carbon atoms.

21. A process for the preparation of oligomers, comprising the following steps:
   (a) heat-treating to a moisture content of about 1 wt. % or less an acidic calcium montmorillonite clay having a moisture content prior to heat treatment ranging up to about 20 wt. % or less, having a residual acidity in the range of about 3 to about 30 mg KOH/g, and a surface area of about 300 M²/g or greater; and
   (b) contacting a mixture of propylene and an alpha-olefin having from 10 to 24 carbon atoms with a catalytically effective amount of said clay.

22. The process of claim 21, wherein the moisture content of the clay prior to heat treatment is about 12 wt. %, the residual acidity is about 8.5 mg KOH/g, and the surface area is about 425 M²/g.

23. The process of claim 21, wherein the moisture content of the clay prior to heat treatment is about 2 wt. %, the residual acidity is about 7.0 mg KOH/g, and the surface area is about 400 M²/g.

24. The process of claim 21, wherein the moisture content of the clay prior to heat treatment is about 16 wt. %, the residual acidity is about 15 mg KOH/g, and the surface area is about 300 M²/g.

25. The process of claim 21, wherein the moisture content of the clay prior to heat treatment is about 4 wt. %, the residual acidity is about 10 mg KOH/g, and the surface area is about 300 M²/g.

26. The process of claim 21, wherein the moisture content of the clay prior to heat treatment is essentially nil, the residual acidity is about 3.0 mg KOH/g, and the surface area is about 350 M²/g.

27. The process of claim 21, wherein the olefin is contacted with the clay at a temperature of about 150° to about 180° C.

28. The process of claim 21, wherein the temperature at which the clay is heat-treated is from 50° to 350° C.

29. A process for the preparation of oligomers, comprising the following steps:
   (a) heat-treating to a moisture content of about 1 wt. % or less an acidic calcium montmorillonite clay having a moisture content prior to heat treatment ranging up to about 20 wt. % or less, a residual acidity in the range of about 3 to about 30 mg KOH/g, and a surface area of about 300 M²/g or greater; and
   (b) contacting a mixture of propylene and an alpha-olefin containing from 12 to 18 carbon atoms with a catalytically effective amount of said clay.

30. The process of claim 29, wherein the moisture content of the clay prior to heat treatment is about 12 wt. %, the residual acidity is about 8.5 mg KOH/g, and the surface area is about 425 M²/g.

31. The process of claim 29, wherein the moisture content of the clay prior to heat treatment is about 2 wt. %, the residual acidity is about 7.0 mg KOH/g, and the surface area is about 400 M²/g.

32. The process of claim 29, wherein the moisture content of the clay prior to heat treatment is about 16 wt. %, the residual acidity is about 15 mg KOH/g, and the surface area is about 300 M²/g.

33. The process of claim 29, wherein the moisture content of the clay prior to heat treatment is about 4 wt. %, the residual acidity is about 10 mg KOH/g, and the surface area is about 300 M²/g.

34. The process of claim 29, wherein the moisture content of the clay prior to heat treatment is essentially nil, the residual acidity is about 3.0 mg KOH/g, and the surface area is about 350 M²/g.

35. The process of claim 29, wherein the olefin is contacted with the clay at a temperature of about 50° to about 180° C.

36. The process of claim 29, wherein the alpha-olefin contains from 13 to 16 carbon atoms.

37. The process of claim 29, wherein the temperature at which the clay is heat treated is from 50° to 350 ° C.

38. A process for preparing a synthetic lubricant component, comprising: co-oligomerizing a mixture of propylene and an alpha-olefin having from 10 to 24 carbon atoms, in which the mixture of propylene and alpha-olefin is comprised of up to about 20 wt. % propylene, by contacting said mixture with a catalytically effective amount of ah acidic calcium montmorillonite clay having a moisture content ranging up to about 20 wt. %, a residual acidity in the range of about 3 to about 30 mg KOH/g, and a surface area of about 300 M²/g or greater; removing any remaining un-oligomerized olefin; and hydrogenating the resulting oligomer fraction to produce a synthetic lubricant component.

39. The process of claim 38, wherein the alpha-olefin contains from 12 to 18 carbon atoms.

40. The process of claim 38, wherein the mixture of propylene and alpha-olefin is comprised of about 2 to about 10 wt. % propylene.

* * * * *